United States Patent
Mestha et al.

(10) Patent No.: US 7,307,720 B2
(45) Date of Patent: Dec. 11, 2007

(54) METHOD FOR CORRECTED SPECTROPHOTOMETER OUTPUT FOR MEASUREMENTS ON MULTIPLE SUBSTRATES

(75) Inventors: Lalit K. Mestha, Fairport, NY (US); Miroslav B. Bartik, San Antonio, TX (US)

(73) Assignee: Xerox Corporation, Norwalk, CT (US)

( * ) Notice: Subject to any disclaimer, the term of this patent is extended or adjusted under 35 U.S.C. 154(b) by 371 days.

(21) Appl. No.: 11/093,446

(22) Filed: Mar. 29, 2005

(65) Prior Publication Data
US 2006/0221337 A1 Oct. 5, 2006

(51) Int. Cl.
*G01J 3/42* (2006.01)
*G01N 21/25* (2006.01)

(52) U.S. Cl. .................. 356/319; 356/300; 702/85; 702/104

(58) Field of Classification Search ................ 356/300, 356/319, 326, 328; 702/85, 104
See application file for complete search history.

(56) References Cited

U.S. PATENT DOCUMENTS

| 6,384,918 | B1 | 5/2002 | Hubble, III et al. | 356/402 |
| 6,539,323 | B2 * | 3/2003 | Olson | 356/402 |
| 2003/0050768 | A1 | 3/2003 | Mestha et al. | 702/196 |
| 2003/0055575 | A1 | 3/2003 | Viassolo et al. | 702/27 |
| 2003/0055611 | A1 | 3/2003 | Mestha et al. | 702/196 |

* cited by examiner

*Primary Examiner*—F. L. Evans
(74) *Attorney, Agent, or Firm*—Richard H. Kruker; Luis M. Ortiz; Kermit D. Lopez

(57) ABSTRACT

Small, fast, and inexpensive in-line spectrophotometers can produce in-line spectrums of a substrate before or after printing on the substrate. In-line spectrums are generally far less complete than a reference spectrum produced with a large, slow, and expensive reference spectrophotometer. An in-line spectrum can be mapped to a reference spectrum using a variety of known algorithms. However, the mapping is erroneous when the media substrate type changes. Reference transform matrices and in-line transform matrices can correct the erroneous mapping.

20 Claims, 4 Drawing Sheets

METHOD FOR CORRECTED SPECTROPHOTOMETER OUTPUT FOR MEASUREMENTS ON MULTIPLE SUBSTRATES

TECHNICAL FIELD

Embodiments relate to the areas of printing and xerography. Embodiments also relate to correcting measurements produced by in-line sensors that can be placed inside printing machines or xerographic machines. The sensors can measure the reflected spectrum of a substrate before printing and after printing.

BACKGROUND OF THE INVENTION

Printers, copiers, and xerographic machines are machines that produce a pattern on a substrate. Typically they consist of a means of obtaining the desired pattern and a marking engine that fixes the pattern to a substrate. Paper, cloth, and plastic are examples of substrates. A pattern can be fixed to a substrate using ink, pigment, or a similar material. Precise control is required to ensure that the pattern produced by the marking engine is acceptably similar to the desired pattern. Over time, the marking engine can experience unintentional change because its mechanical components can change, the ink can change, and the substrate can change. To compensate for unintentional change, a controller can make intentional changes to the marking process such that the marking engine produces a consistent product.

In performing its function, a controller runs control algorithms and needs control inputs and outputs. An ideal control input for a marking engine controller is the reflectance spectrum of printed materials. A spectrophotometer can be used to produce a reflectance spectrum. An in-line spectrophotometer is a device that can be used for monitoring and control of production processes such as printing and copying. A spectrophotometer that can be used as an in-line spectrophotometer is disclosed in U.S. Pat. No. 6,384,918, which is incorporated herein by reference. Utilized as an in-line sensor, an aspect of the disclosed spectrophotometer produces a measurement, called an in-line spectrum that consists of the reflectance measured at eight different wavelengths. Other types of in-line spectrophotometers can also produce in-line spectrums and those in-line spectrums can have a different number of reflectance measurements made at different wavelengths.

In many applications, a spectrum that includes at least 30 different wavelengths is desired. A well-calibrated and precise spectrophotometer or a similar device, hereinafter called a reference spectrophotometer, can make the desired measurement, hereinafter called a reference spectrum. Reference spectrophotometers typically cannot be used in-line because they tend to be large expensive and slow. A close approximation of a reference spectrum, called a reconstructed spectrum, can be calculated from an in-line spectrum using methods disclosed in U.S. patent application publications numbers 20030050768, 20030055611, and 20030055575. The disclosed methods produce a reconstruction matrix that maps an in-line spectrum to a reconstructed spectrum. The referenced methods use an in-line spectrum and a reference spectrum to produce a reconstruction matrix, but thereafter use in-line spectrums and the reconstruction matrix to produce corrected spectrums.

Current art teaches systems and methods by which a reconstructed spectrum having the quality of a reference spectrum can be produced from an in-line spectrum and a reconstruction matrix when the substrate does not change. In the real world, substrates do change. For example, a specific type of paper used as a printing substrate can change between manufacturing batches. Another example is that two versions of a publication can be printed, one on a high quality paper and the other on a low quality paper. Substrate changes cause the reconstruction matrix to become inaccurate. The reason is because the reflectance spectrum of printed material depends on the reflectance spectrums of both the substrate and the printed pattern and because different types of substrates can have significantly different reflectance spectrums. Prior methods and systems produce excellent results as long as the substrate does not change.

Linear algebra, which includes vector and matrix manipulations, is well known. The prior art and the present embodiment are presented via linear algebraic notation. A few of these notations are of particular interest. One is the diag() function that transforms an M element vector into an M by M matrix with the vector elements on the main diagonal of the matrix. Another is the matrix inverse. A matrix multiplied by its own matrix inverse results in an identity matrix. Another concept is the distance between two vectors. One common measure is the Euclidean distance. Given two vectors with two elements, (a, b) and (c, d), the Euclidean distance is sqrt((a−c)*(a−c)+(b−d)*(b−d)), where sqrt( ) is the square root function. Other distance measures such as the Mahalinobis distance, or absolute difference are also common.

The embodiments described herein therefore overcome the aforementioned limitations and flaws of the prior art.

BRIEF SUMMARY

Aspects of the embodiments address limitations and flaws in the prior art by using transform matrices on the reconstruction matrix and thereby correct for substrate changes.

It is therefore one aspect of the embodiments provide for obtaining a target in-line spectrum from a target substrate and identifying the substrate type of the target substrate. A target substrate is a substrate that can be patterned by a marking engine. A "substrate type" refers to a general class of substrates that have the same properties. For example, if a manufacturer produces printable plastic substrates that are consistent from batch to batch, then all the plastic substrates from that manufacturer are of the same substrate type. If another manufacturer produces significantly similar substrates, then all the plastic substrates from both manufacturers would be of the same substrate type.

It is another aspect of the embodiments to provide for retrieving data from a storage device wherein the specific data retrieved is based on the substrate type of the target substrate.

It is a further aspect of the embodiments to provide for producing a corrected spectrum from the retrieved data and the target in-line spectrum.

BRIEF DESCRIPTION OF THE DRAWINGS

The accompanying figures, in which like reference numerals refer to identical or functionally similar elements throughout the separate views and which are incorporated in and form a part of the specification, further illustrate the present invention and, together with the background of the invention, brief summary of the invention, and detailed description of the invention, serve to explain the principles of the present invention.

In accordance with one aspect of the embodiments.

In accordance with another aspect of the embodiments.

In accordance with yet another aspect of the embodiments.

DETAILED DESCRIPTION

The particular values and configurations discussed in these non-limiting examples can be varied and are cited merely to illustrate embodiments that are not intended to limit the scope of the invention.

Figure 1:
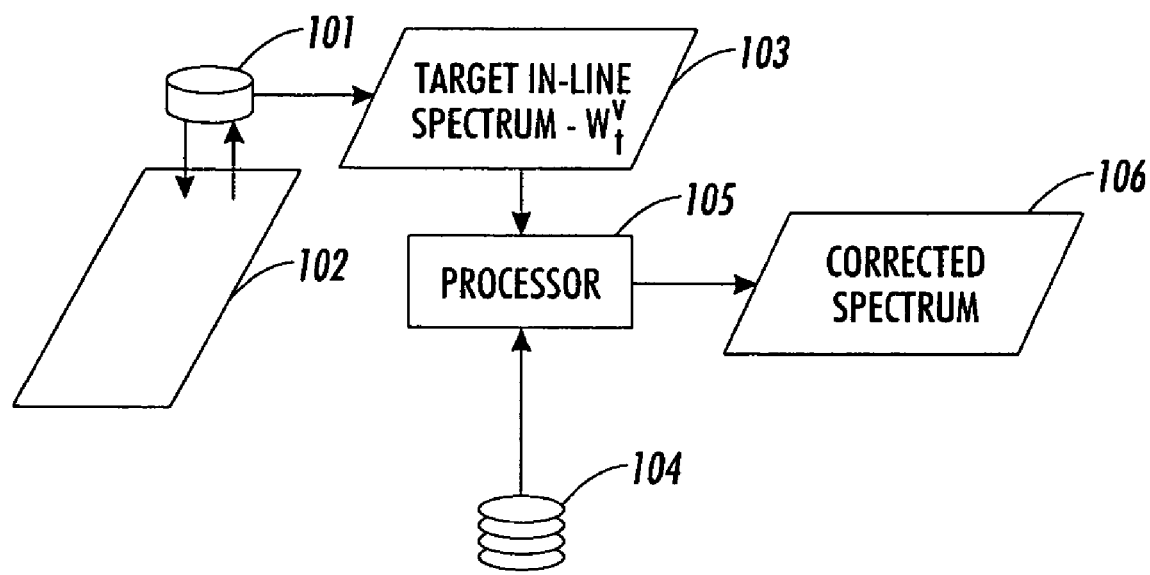
FIG. 1 illustrates production of a corrected spectrum.

FIG. 1 illustrates production of a corrected spectrum. An in-line spectrophotometer 101 produces a target in-line spectrum 103 by measuring the reflectance spectrum of a target substrate 102. The target in-line spectrum 103 is mathematically represented by $w_t^v$ where t means target and v means in-line. A processor 105 uses the target in-line spectrum 103 and data retrieved from a storage device 104 to produce a corrected spectrum 106.

Figure 2:
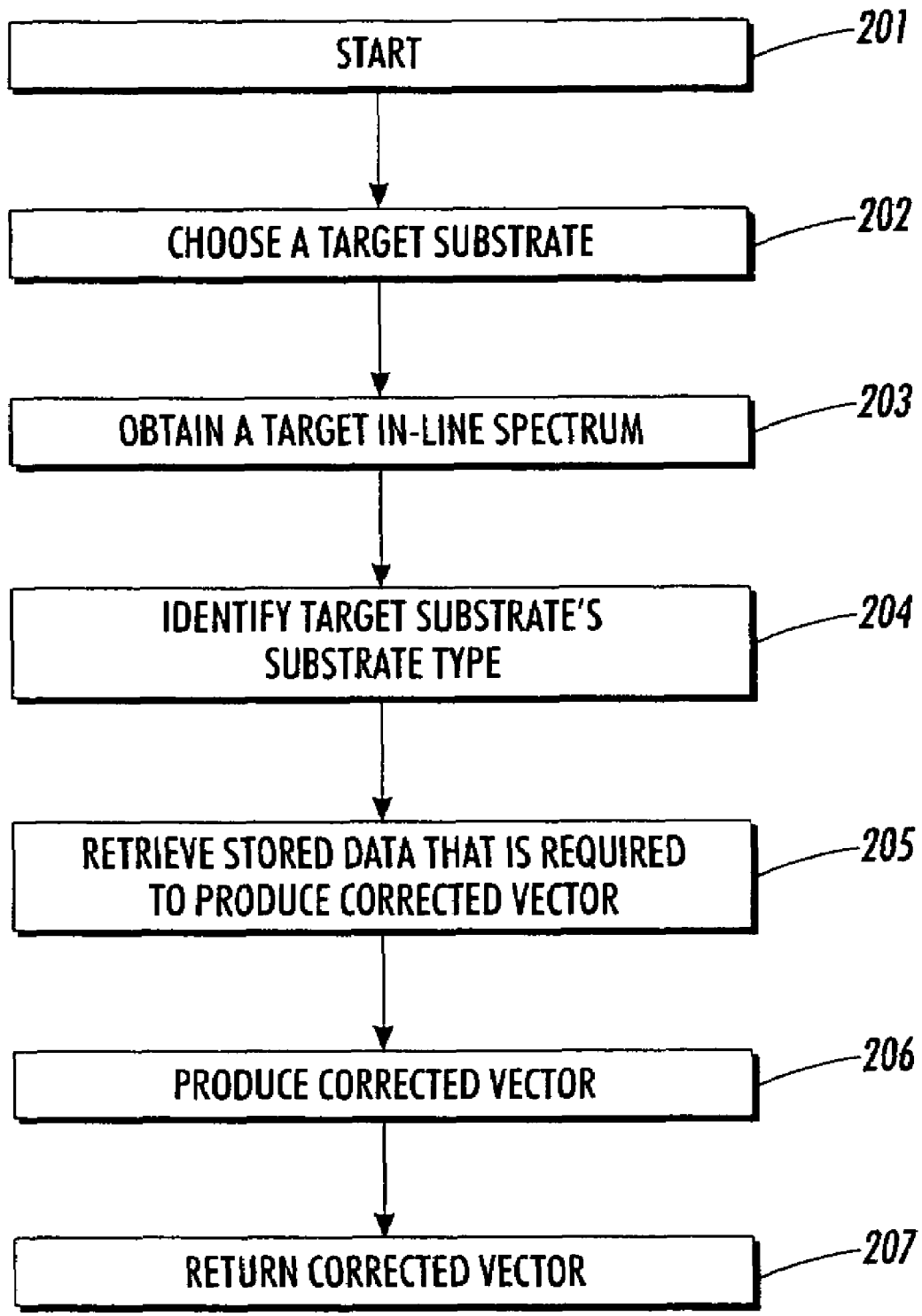
FIG. 2 illustrates a high level flow diagram.

FIG. 2 illustrates a high level flow diagram that can be used in conjunction with the system illustrated in FIG. 1. After the start 201, a target substrate is chosen 202 its target in-line spectrum is obtained 203. The substrate type of the target substrate is identified 204 and used to retrieve data that can be used to produce a corrected vector 205. The target in-line spectrum and retrieved data are used to produce a corrected vector is produced 206 that is returned 207.

Figure 3:
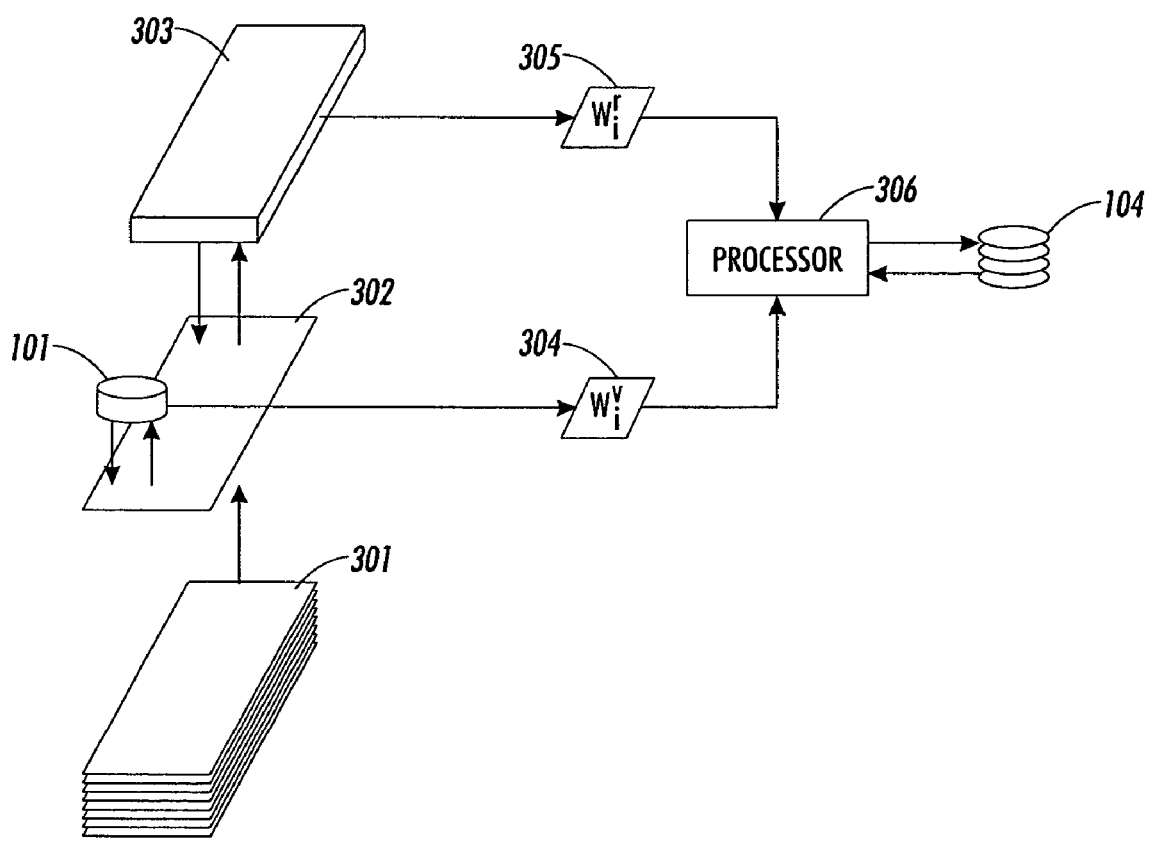
FIG. 3 illustrates production and storage of data that can be used for producing a corrected spectrum; and In accordance with a further aspect of the embodiments.

FIG. 3 illustrates production and storage of data that can be used for producing a corrected spectrum. A representative substrate 302 that is typical of the ith substrate type 301 is chosen. A reference spectrophotometer 303 measures the representative substrate's reflectance spectrum to produce a representative reference spectrum 305. An in-line spectrophotometer 101 measures the representative substrate's reflectance spectrum to produce a representative in-line spectrum 304.

The representative reference spectrum 305 is mathematically represented by $w_i^r$ where r means reference and i means the representative reference spectrum is associated with the ith substrate type 301. The representative in-line spectrum 304 is mathematically represented by $w_i^v$ where v means in-line and i means the in-line reference spectrum is associated with the ith substrate type 301.

A processor 306 takes the representative reference spectrum 305 and the representative in-line spectrum 304 and uses them to produce data that is stored on a storage device 104. The data can be used, along with a target in-line spectrum, to produce a corrected spectrum.

Figure 4:
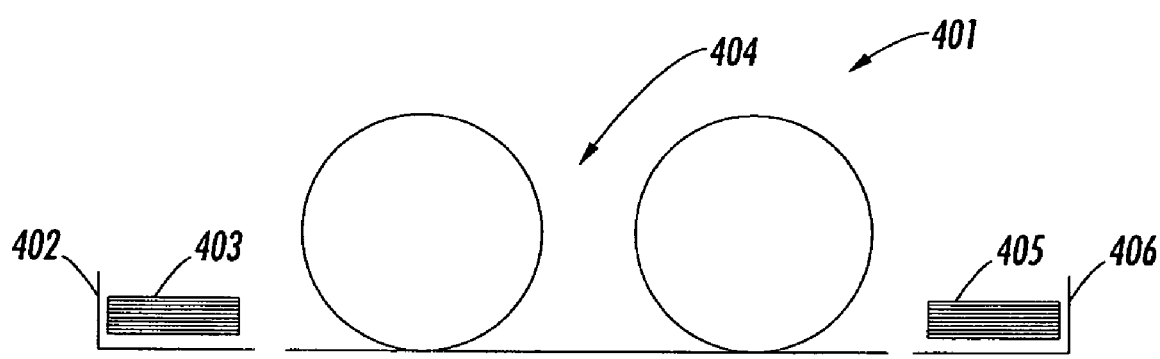
FIG. 4 illustrates components of a marking engine.

FIG. 4 illustrates components of a marking engine 401. Printable substrates 403 can be supplied to the marking engine 401 via an input port 402. Substrates can be moved from the input port 402 to a marking apparatus 404 that produces patterns on the substrate. The patterned substrates 405 can then be collected in an output port 406. The substrates in FIG. 4 are shown as stacked sheets. A substrate can also be presented in an input port 402 in rolled form where hundreds of feet of substrate are rolled into a cylinder. Substrates can also be rolled up at the output port 406.

A spectrophotometer measures a spectrum by measuring the spectrum at many different wavelengths. Essentially, the spectrophotometer makes many measurements, each at a different wavelength, and combines the measurements into a vector called a spectrum.

The number of different wavelengths measured by a reference spectrophotometer is denoted M. The first reference wavelength can be expressed as $\lambda_1^r$ and the last reference wavelength can be expressed $\lambda_M^r$. Each individual measurement is a function of wavelength. The measurement of a representative substrate made at the first reference wavelength can be expressed as $w_i^r(\lambda_1^r)$. The measurement of a representative substrate made at the last reference wavelength can be expressed as $w_i^r(\lambda_M^r)$. A representative reference spectrum can be expressed as $w_i^r = |w_i^r(\lambda_1^r) w_i^r(\lambda_2^r) \ldots w_i^r(\lambda_M^r)|^T$ where T indicates transpose. The subscripted i is used to indicate the substrate type of the representative substrate.

An in-line spectrophotometer makes measurements at N different wavelengths. The first in-line wavelength can be expressed as $\lambda_1^v$ and the last reference wavelength can be expressed as $\lambda_N^v$. As such, a representative in-line spectrum can be expressed as $w_i^v = |w_i^v(\lambda_1^v) w_i^v(\lambda_2^v) \ldots w_i^v(\lambda_N^v)|^T$. Similarly, a target inline spectrum can be expressed as $w_t^v = w_t^v(\lambda_1^v) w_t^v(\lambda_2^v) \ldots w_t^v(\lambda_N^v)|_T$ where the subscripted t means target.

A corrected spectrum can be calculated as $w_t^c = T_i^r A T_i^v W_t^v$ where $T_i^r$ is the reference transform matrix, $T_i^v$ is the in-line transform matrix, A is the reconstruction matrix, and $W_t^c$ is the corrected spectrum.

The reference transform matrix can be calculated as $T^r = \text{diag}(w_i^r)(\text{diag}(w_1^r))^{-1}$ and the inline transform matrix can be calculated as $T_i^v = \text{diag}(w_1)(\text{diag}(w_1^v))^{-1}$ where the superscripted −1 indicates the matrix inverse and diag( ) is the well known function that converts a M point vector into an M by M matrix such that the main diagonal contains the vector elements. There are numerous methods known for obtaining the reconstruction matrix.

The equation for $T_i^r$ includes the term $w_1^r$ where the subscripted i is replaced with a subscripted 1 meaning that the representative reference spectrum is associated with the first substrate type. If there were only one substrate type, then there would be no error introduced by changes in substrate. When there is more than one substrate type, then one of them is referred to as the first substrate type. Therefore, $w_1^r$ refers to the reference spectrum associated with the first substrate type. Similarly $w_1^v$ that appears in the equation for $T_i^v$ refers to the in-line spectrum associated with the first substrate type. The first substrate type is typically the one used for producing the reconstruction matrix, A.

A corrected spectrum can also be calculated as $w^c = T_i^r A T_t^v w_t^v$ where $T_t^v$ is the target transform matrix. The target transform matrix can be calculated as $T_t^v = \text{diag}(w_1^v)(\text{diag}(w_t^v))^{-1}$.

The storage device 104 of FIG. 1 and FIG. 2 stores data that can be used to produce a corrected spectrum. Based on the equations given above, all the storage device needs to store is the reconstruction matrix, the representative reference spectrums associated with every substrate type, and the representative in-line spectrums associated with every substrate type.

It can be seen from the equations that all the information required for calculating the reference transform matrix is known before any target in-line spectrum is obtained. As such, the reference transform matrix associated with each substrate type can be calculated and stored in the data storage device. This is known as pre-calculation and is a common technique for more quickly obtaining numerical results. As such, the processor 105 can retrieve the reference transform matrix associated with the target substrate's substrate type instead of retrieving the representative reference spectrum.

By a similar argument, the in-line transform matrix can also be pre-calculated and stored. However, the representative in-line spectrums must also be stored if they are used for finding the target substrate's substrate type.

Another observation is that the reconstruction matrix is also known before any target substrate is measured. From the equations, numerous opportunities for pre-calculation and storage present themselves. In general, a numerical result involving the any combination of a reference transform matrix, the reconstruction matrix, and an in-line transform matrix can be pre-calculated and stored.

When the in-line spectrum of a target substrate is obtained, the target substrate's substrate type must be identified. One easy, but unreliable, way to identify it is to simply ask the user. It can also be identified by comparing the target in-line spectrum to every in-line spectrum stored by the storage device and choosing the substrate type associated with the most similar representative spectrum.

Two spectrums can be compared using any of the known methods that are used to compare two vectors for similarity. Such methods include the Euclidean distance and Mahalinobis distance. Similarly, the known techniques for pattern recognition It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method comprising:
   obtaining a target in-line spectrum from a target substrate and identifying the substrate type of the target substrate;
   retrieving data from a storage device wherein the specific data retrieved is based on the substrate type of the target substrate; and
   producing a corrected spectrum from the retrieved data and the target in-line spectrum.

2. The method of claim 1 further comprising:
   retrieving representative in-line spectrums from the data storage device; using the Euclidean distance to find the representative in-line spectrum closest to the target in-line spectrum; and
   identifying the substrate type associated with the closest representative in-line spectrum as the target substrate's media substrate type.

3. The method of claim 1 further comprising:
   retrieving representative in-line spectrums from the data storage device; using the Mahalinobis distance to find the representative in-line spectrum closest to the target in-line spectrum; and
   identifying the substrate type associated with the closest representative in-line spectrum as the target substrate's media substrate type.

4. The method of claim 1 further comprising accepting user input to identify the substrate type.

5. The method of claim 1 wherein the data retrieved from the storage device comprises one or more representative reference spectrum.

6. The method of claim 1 wherein the data retrieved from the storage device comprises one or more representative in-line spectrum.

7. The method of claim 1 wherein the data retrieved from the storage device comprises one or more representative reference transform matrix.

8. The method of claim 1 wherein the data retrieved from the storage device comprises one or more representative in-line transform matrix.

9. The method of claim 1 wherein the data retrieved fmm the storage device comprises a reconstruction matrix determined by using a dynamic least squares algorithm.

10. The method of claim 1 wherein a representative in-line transform matrix is used to produce the corrected spectrum.

11. The method of claim 1 wherein a target in-line transform matrix is used to produce the corrected spectrum.

12. A method comprising:
    obtaining a representative in-line spectrum and a representative reference spectrum from a representative substrate that is typical of a substrate type;
    using the in-line spectrum and reference spectrum to produce data for later use in producing a corrected spectrum; and
    storing the data in a storage device.

13. The method of claim 12 wherein the data stored in the storage device comprises the representative in-line spectrum.

14. The method of claim 12 wherein the data stored in the storage device comprises the representative reference spectrum.

15. The method of claim 12 wherein the data stored in the storage device comprises a representative reference transform matrix.

16. The method of claim 12 wherein the data stored in the storage device comprises the representative in-line transform matrix.

17. A system comprising:
    a data storage device that holds data that is used to produce a corrected spectrum;
    a measurement device the produces an in-line spectrum;
    a processor that uses the data retrieved from the storage device and the in-line spectrum to produce a corrected spectrurm; and
    wherein the measurement device is positioned so as to measure the in-line spectrum of material in either or both of a marking engine's input port or output port.

18. The system of claim 17 wherein the measurement device is a spectrophotometer.

19. The system of claim 17 wherein the measurement device is positioned so as to measure the in-line spectrum of material in the marking engine's input port.

20. The system of claim 17 wherein the measurement device is positioned so as to measure the in-line spectrum of material in the marking engine's output port.

* * * * *